United States Patent
Klein et al.

(10) Patent No.: US 6,514,773 B1
(45) Date of Patent: Feb. 4, 2003

(54) METHOD OF DETECTING SURFACE CONTAMINATION BY AN ANALYTE

(75) Inventors: Christian Klein, Weilheim (DE); Hans-Peter Josel, Weilheim (DE); Ada Goerlach-Graw, Grosskarlbach (DE); Reinhold Hilpert, Moorenweis (DE); Florian Binder, Traunstein (DE); Josef Ritter, München (DE); Rudolf Zimmermann, Vagen (DE)

(73) Assignee: Securetec Detektions-Systeme AG, Ottobrunn (DE)

(*) Notice: Subject to any disclaimer, the term of this patent is extended or adjusted under 35 U.S.C. 154(b) by 1519 days.

(21) Appl. No.: 08/506,268

(22) Filed: Jul. 24, 1995

(30) Foreign Application Priority Data

Jul. 25, 1994 (DE) .......................... 44 26 281
Nov. 4, 1994 (DE) .......................... 44 39 429

(51) Int. Cl.[7] .................. G01N 33/544; G01N 33/558; G01N 33/543; G01N 33/553
(52) U.S. Cl. ................ 436/528; 436/514; 436/518; 436/525; 436/535; 436/809; 436/810; 435/4; 435/7.1
(58) Field of Search ................ 436/514, 518, 436/525, 528, 535, 809, 810; 435/4, 7.1

(56) References Cited

U.S. PATENT DOCUMENTS

| | | | |
|---|---|---|---|
| 4,861,711 A | 8/1989 | Friesen et al. | |
| 4,968,633 A | 11/1990 | Marcucci | |
| 5,113,860 A | 5/1992 | McQuinn | 128/632 |
| 5,118,609 A * | 6/1992 | Baier et al. | 435/7.9 |
| 5,120,643 A | 6/1992 | Ching et al. | |
| 5,141,850 A | 8/1992 | Cole et al. | |
| 5,169,789 A | 12/1992 | Bernstein | |
| 5,182,191 A | 1/1993 | Fan et al. | |
| 5,250,412 A * | 10/1993 | Giegel | 435/7.1 |
| 5,415,994 A | 5/1995 | Imrich et al. | |
| 5,416,000 A | 5/1995 | Allen et al. | |
| 5,451,504 A * | 9/1995 | Fitzpatrick et al. | 435/7.2 |
| 5,766,962 A | 6/1998 | Childs et al. | |

FOREIGN PATENT DOCUMENTS

| | | |
|---|---|---|
| CA | 1268420 | 5/1990 |
| CA | 2005564 | 6/1990 |
| CA | 5047691 | 9/1990 |
| CA | 1289070 | 9/1991 |
| CA | 1303493 | 6/1992 |
| CA | 2109090 | 10/1992 |
| EP | 0 262 328 | 4/1988 |
| EP | 0 339 450 | 11/1989 |
| EP | 0 436 897 | 7/1991 |
| EP | 0 440 350 | 8/1991 |
| WO | WO 94/25945 | 11/1994 |
| WO | WO 95/27205 | 10/1995 |

OTHER PUBLICATIONS

Abstracts of Security Management vol. 37/8 pp. 12–15, 1993.
Security Management, It's not a boy vol. 37/8, No. 8, 1993, pp. 12–15.

* cited by examiner

Primary Examiner—Rodney P Swartz
(74) Attorney, Agent, or Firm—Arent Fox Kintner Plotkin & Kahn, PLLC

(57) ABSTRACT

Subject matter of the invention is a method for detecting surface contamination by an analyte by wiping the analyte off the surface with the aid of a wiping surface, eluting the analyte from the wiping surface with an eluant, and detecting the analyte in the eluate in an immunological detection reaction, characterized in that:

a) the surface to be tested for the analyte is wiped with a wiping surface, b) the wiping surface is brought into contact with the planar surface of a capillary active, chromatographic test strip which has an eluant application zone at its one end and a target zone at its other end whereby contact is made in an area between these two zones, c) eluting liquid is applied onto the zone provided for this purpose, said liquid moving toward the target zone passes the contact site with the wiping surface as a consequence of capillary forces, whereby analyte is taken up by the eluant, and d) in the target zone, the analyte is measured in an immunological binding reaction.

The method is particularly suitable for the detection of drugs on surfaces.

25 Claims, 2 Drawing Sheets

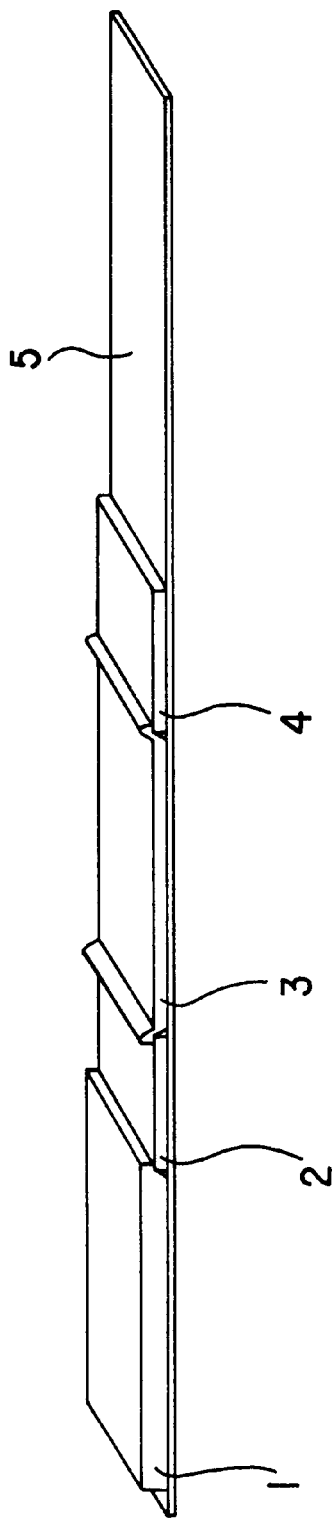
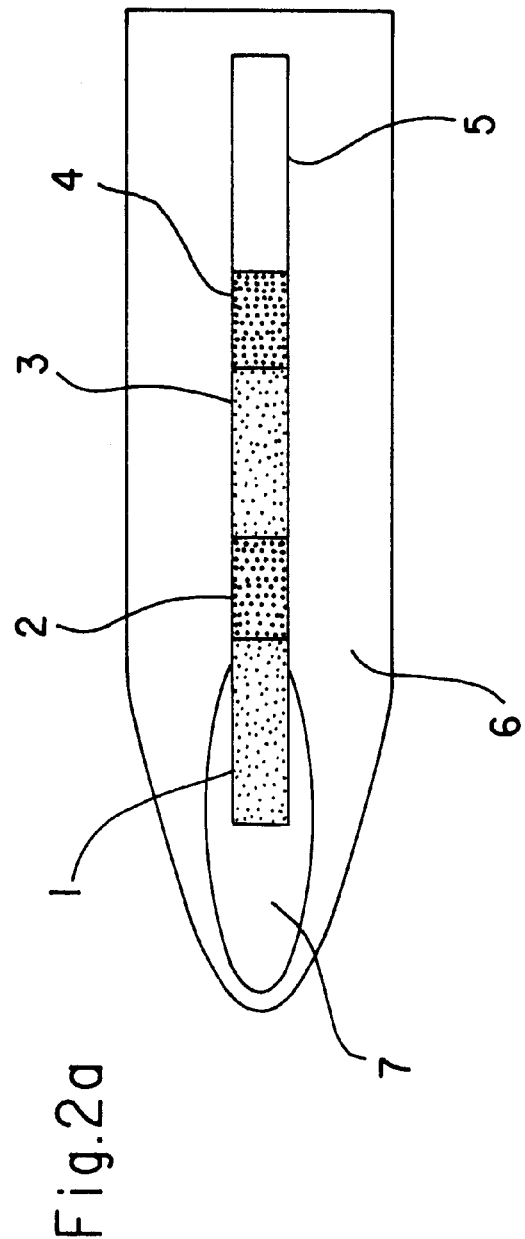

METHOD OF DETECTING SURFACE CONTAMINATION BY AN ANALYTE

The invention addresses a method of detecting surface contamination by an analyte by wiping the analyte off the surface with the aid of a wiping surface, eluting the analyte from said wiping surface and detecting the analyte in the eluate in an immunological detection reaction. Moreover, the invention also addresses a corresponding analysis element.

In addition to the detection of analytes in sample liquids, such as blood, urine, saliva, the detection of analytes on solid surfaces such as furniture and baggage has gained increasingly more importance in criminal sciences. Especially in the fight against drugs, it is desirable to have a simple and rapid way of detecting even very small amounts of drugs on objects. With an increased degree of sensitivity of the detection, it is, of course, possible to detect even smaller amounts of analyte on a given contaminated surface.

In order to test for analytes, especially drugs, on any desired surface, various special detection techniques are known where the analyte is first collected by wiping the surface and then immunologically detecting after eluting, the analyte from the surface used for the wiping. In case of the "Illicit Substance Detector" manufactured by Westinghouse, Baltimore, USA (Security Management, Vol. 37/8, pages 12–15, 1993), the surface to be examined is wiped with a napped plastic material, and the drug is detected via a method with three reagent solutions that are integrated in a disposable card (DE-A-4341862). The test result is evaluated with an optical reader. The principle of this immunological detection is based on the inhibition of a latex agglutination reaction by the drug to be detected. The lower detection limit is indicated in micrograms. Despite the high detection limit, it is a disadvantage that the detection reaction must be started by mechanically squeezing the three liquid reservoirs. Moreover, the result can only be evaluated with an optical reader and not with the bare eye.

Roche Diagnostics is the manufacturer of a test kit to detect cocaine from urine samples according to the same complex immunological detection principle. The sensitivity of this detection ranges around 0.2 µg/ml.

The "Accupress Kit" manufactured by Thermetics, Woburn, USA (Security Management, Vol. 37/8, pages 12–15, 1993) comprises a reagent carrier having a special coating and three vessels containing reagent solutions. In this test, the surface to be examined is wiped with a cotton swab; and the swab is then washed with buffer. In addition to the comparable insensitive detection limit of not below 1 µg, the handling of these three different reagent solutions is also inconvenient and is a source of errors.

It was, hence, an object of the invention to provide a more sensitive method of detecting analyte contamination of surfaces, especially traces of drugs, which can be carried out in a simple manner and without technical support means. Especially the detection limit for the analyte should be significantly below 1 µg, absolutely, and if possible below 100 ng.

This object is accomplished with a method and analysis element as characterized in the claims.

Subject matter of the invention is a method of detecting surface contamination by an analyte by wiping the analyte off the surface with a wiping surface, eluting said analyte from the wiping surface and detecting the analyte in the eluate in an immunological assay, is characterized in that a) the surface to be tested for the analyte is wiped with the wiping surface, b) the wiping surface is brought into contact with the planar surface of a capillary, chromatographic test strip which, at its one end, has an application zone for applying an eluant liquid and, at its other end, a target zone, whereby contact is made in an area between these two zones, c) eluant liquid is applied onto the application zone, said liquid moving toward the target zone passing the contact site with the wiping surface as a consequence of capillary forces, whereby analyte is absorbed by the eluant, and d) in the target zone, the analyte is measured in an immunological binding reaction.

The test strip for the method in accordance with the invention can be made of one single chromatographic strip-like material, or preferably several capillary surfaces made of the same or different materials and disposed on a base layer are essentially arranged next to one another. Said surfaces are in a fluid contact to each other so as to form a transport path along which a liquid driven by capillary forces flows from the eluant application zone toward the target zone.

Possible chromatographic materials are all liquid-absorbent, porous, or capillary active materials, such as cellulose or its derivatives, glass fiber, and fleeces, and fabrics made of synthetic or natural materials.

BRIEF DESCRIPTION OF THE DRAWINGS

FIG. 1 shows a chromatography test strip including an eluant application zone(1), a conjugate zone (2), a capture zone (3), a target zone (4), and a carrier foil (5).

FIG. 2a shows the test carrier of the present invention in a housing without the cover.

Figure 2B:
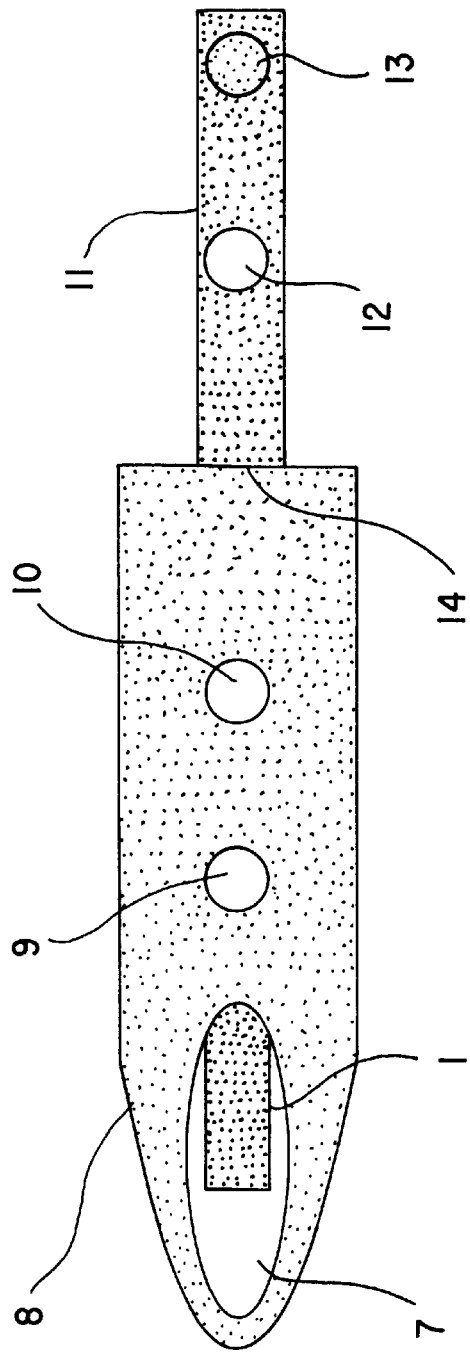
FIG. 2b shows the test carrier of the present invention in a housing (8) which is closed and the wiping material (13) which is provided on a carrier (11) fixed to a hinge of the housing. An opening (12) in the carrier (11) allows monitoring of the signal. The sample collecting element (13) is attached to the carrier (11) which is secured to a hinge (14) of carrier (11) so that the carrier can be opened out or flipped over.

In the method of the invention, it is possible to make use of different immunological testing procedures to detect the analyte based on one or several immunological binding reactions. In a preferred embodiment (FIG. 1), a chromatography test strip suitable for the purpose of the invention contains a capture zone (3) containing an immobilized capture reagent. Said zone (3) is provided on a carrier foil (5) between the eluant application zone (1) and the target zone (4). Said immobilized capture agent is capable of specifically binding either the analyte, a specific binding partner of the analyte, or a labeled binding partner. A conjugate zone (2) containing a labeled binding partner that is able to migrate precedes the capture zone on the test strip. Said labeled binding partner is capable of specifically binding either the analyte, a specific binding partner of the analyte, or the capture reagent in the capture zone.

The "specific binding partner of the analyte" is an unlabeled analyte binding partner that is able to migrate and has a binding site for the capture reagent. If such a binding partner is used in an immunoassay, it can be applied before or in the conjugate zone, or preferably between the conjugate zone and the capture zone. In addition, a liquid-absorbing material may be provided after the target zone to absorb liquid after migration through the individual zones.

Depending on the type of immunoassay used in the method of the invention, different binding partners are present in the different zones: In a sandwich immunoassay, it is preferred to have a labeled, non-immobilized analyte-binding partner in the conjugate zone. This analyte-binding partner forms a complex together with the analyte which is bound by the capture reagent by binding to the analyte; or it is possible that a second unlabeled analyte-binding partner that is free to migrate and has a specific binding site for the capture reagent forms a sandwich complex with the analyte. Said complex is then bound in the capture zone through the specific binding site of the binding partner. In a preferred manner, the label of the complex is determined in the capture zone. In this case, capture zone and target zone are identical.

In a competitive test, it is preferred to have a labeled analyte analog in the conjugate zone. When an analyte is present, said analog competes for the binding sites of the capture reagent in the capture zone (in this case the capture reagent is an analyte-binding partner), or, in the presence of an additional analyte-binding partner that is able to migrate, it competes for the binding site thereof So formed complexes of labeled analyte analog and migrating binding partner are bound in the capture zone via a specific binding site, e.g. biotin. In this case, the capture reagent is a binding partner of the migrating analyte-binding partner, e.g. streptavidin. In a preferred manner, the label in this method is not measured in the capture zone, but in the target zone in the form of a non-complexed analyte analog as a measure for the amount of analyte.

In a preferred manner, the method of the invention is carried out according to an IEMA-analog test principle (also known as immunoenzymometric-assay-analog test principle). The implementation of IEMA tests on test strips is described in U.S. Pat. No. 5,188,939 or U.S. Pat. No. 5,403,706, EP-A-0 353 570, or DE OS 4024919, for example.

In the conjugate zone, there is an excess amount of labeled binding partner for the analyte. After chromatographic migration, labeled binding partners that are not bound to the analyte are immobilized in the capture zone through the solid-phase bound analyte analog. Complexes of analyte and labeled binding partner continue to migrate to the target zone. The label arriving at the target zone can be determined as a measure for the presence or the concentration of analyte.

In the present invention, possible analytes are all immunologically detectable substances, in particular antigens and haptens. The present invention is particularly suitable for the detection of drugs, such as cocaine, morphines, and heroine. The analyte may be present on the surface to be wiped in the form of molecules or particles or adsorbed to particles.

Possible labels are conventional labels, such as enzyme labels, fluorescent or dye labels. Particularly preferred are direct labels, especially metal labels, and more particularly gold labels. The advantage thereof is that the test result can be directly read with the bare eye.

Possible binding partners for th e analyte are in particular antibodies and a n tibody fragments.

If a migrating unlabeled analyte-binding partner is used additionally to the capture reagent, it has a binding site for the capture reagent. Possible binding sites are all specific binding partners of a specific binding pair, e.g. lectins, antibodies, antigens, preferably biotin (which binds to streptavidin). The label in the capture zone or target zone can be detected with conventional detection methods, e.g. with a reflectance photometer or visually. When metal labels are used, e.g. gold label, it is particularly simple to read off the measurement visually.

Figure 3:
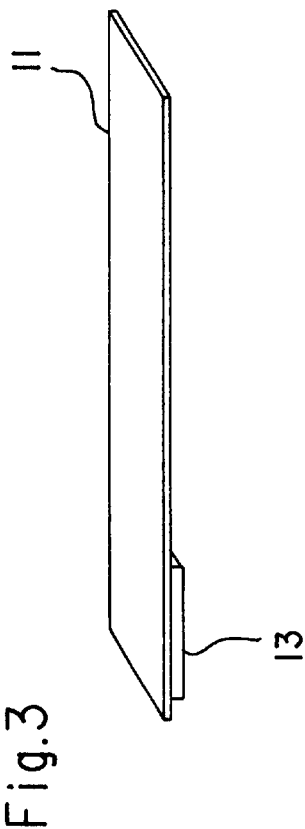
FIG. 3 shows the wiping surface (13) attached to carrier (11).

In order to implement the method of the invention, a surface to be examined is wiped with a wiping surface while advantageously applying slight pressure. The surface to be examined can be dry or covered with an analyte-containing film. It is advantageous to repeat the wiping several times. For a better handling, the wiping surface (13) is preferably attached to a carrier (11) (FIG. 3). There is an especially good wiping success when the wiping material tolerates a high mechanical demand. It has been found that is especially advantageous therefor when the wiping material is attached to the carrier by ultrasonic welding.

Possible materials for wiping surfaces are all materials such as plastics, fabrics, or fleeces to which analytes, especially drugs, adhere and where they can be accumulated by wiping. On the other hand, the analytes adhering thereto should be easy to desorb upon contact with liquid. A skilled person is familar with suitable materials and can choose them easily. Absorbing materials such as fleeces, fabrics, or porous matrices, such as membranes or sponges are preferred. Particularly suitable are fleeces made of a fibrous material, said fibers being generally not present in any order, e.g. paper or glass fiber fleeces. It is preferred to have a dry wiping surface, but it may also be slightly wet.

If rough surfaces, e.g. anodized aluminum surfaces or other rough metal surfaces are examined, it is preferred to have a wet wiping surface. Suitable liquids for wetting the wiping surface are primarily water and aqueous buffer systems which can be adapted to the subsequent immune reaction. The water or the aqueous buffers may contain detergents or organic solvents. Possible detergents are Tween 20, Tween 80, octylglucoside, polidocanol, synperonic, e.g. F 68, but also zwitterionic detergents such as cholamidopropane sulfonate at a concentration below 5 wt. %, preferably at 0.01 wt. % to 1 wt. % alone or in mixtures. Organic solvents include dimethylsulfoxide, glycerin, or ethanol either alone or in mixtures. A percentage of solvents in a liquid may be significantly below 30 weight %. It is, however, also possible to use organic solvents or mixtures of organic solvents without water.

In order to wet the wiping surface, 1–50 $\mu$l of liquid are applied to each $cm^2$ of surface area, preferably 3–20 $\mu l/cm^2$, e.g. with the aid of a pipette or an automated metering device.

Alternatively, it is also possible to wet the wiping surface by bringing it briefly into contact with a wet sponge or another wetting surface.

The wiping surface can advantageously also be wetted by providing the liquid in microcapsules or in blister packs on a part provided for that purpose. If water or aqueous buffer systems are used as liquids, the capsules are advantageously made of wax-like substances, such as paraffin. The liquids are then released mechanically, e.g. by pressing on the surface to be examined.

In a preferred manner, the wiping fleece is made of fibers on the basis of cellulose and/or polyester fibers. In addition, the fibers may be held together by an organic binding agent which preferably contains hydroxyl and/or ester groups. Such fleeces are described in U.S. Pat. No. 5,118,609.

Preferred cellulose fibers are viscous staple fibers, cellulose, or linters. The term viscous staple fibers refers to a material that is obtained by alkalifying cellulose into alkali cellulose, treatment with carbon bisulfide and followed by the formation of cellulose xanthogenates. The cellulose xanthogenates are then dissolved in brine and viscous filament yarns are incorporated by spinning. Cellulose can be obtained through complete chemical digestion of cellulose-containing materials followed by a bleaching process. The term linters refers to short non-spinable cotton fibers there obtained from cotton seeds. Cellulose fibers have a preferred density of 1.7 to 4.5 dtex and a length of 1 to 20 mm, preferably 3 to 12 mm. Particularly preferred polyester fibers are fibers with a specific weight of about 1.17 g/cm$^3$, a length between 3 and 6 mm and a fiber density of 1.7 to 3.3 dtex.

Another component of the fleeces can be an organic binding agent having OH— and/or ester groups. Polyvinyl alcohol or epichlorhydrin resins are preferred. Polyvinyl alcohol is preferably used as a fiber material with a length of 3 to 5 mm and a specific weight of 1.26 to 1.30 g/cm$^3$. These components and fully desalted water are used to produce a fleece on a gravity screen according to conventional methods of paper manufacturing. Particularly preferred fleece materials are also described in U.S. Pat. No. 5,118,609.

The thickness of the wiping surface material is not a critical factor. Advantageously it should have a flat surface with a thickness ranging between 0.1 and 3 mm. The wiping surface should match the dimensions of the chromatography test strip, i.e. the width of the test strip should not significantly exceed the width of the wiping surface. The preferred size of the wiping surface ranges between 0.3 and 2 cm, particularly preferred between 0.5 and 0.8 cm in length and 0.3 to 1 cm in width, particularly preferred between 0.4 and 0.8 cm.

After wiping a contaminated surface with a wiping surface, an area of the test strip surface contacts said wiping surface between the eluant application zone and the target zone, with a slight pressure being preferably applied. This area is preferably located between the eluant application zone and the conjugate zone, or located in the conjugate zone itself. Moreover, it is particularly preferred that the zone onto which the wiping fleece is pressed, be made of a material suitable for the wiping surface, in particular fleece materials as described in U.S. Pat. No. 5,118,609. It is particularly preferred to press the wiping fleece onto the conjugate zone. It is therefore also preferred that the wiping surface covers between 25% and 150% of the area of the conjugate zone, or has essentially the same area as the conjugate zone, the latter being particularly preferred.

The pressure exerted on the wiping surface should be sufficient enough to allow a planar fluid contact between the two surfaces.

In order to facilitate the pressing, the test carrier (5) can be integrated in an housing (6,8) (FIG. 2a: housing with cover, FIG. 2b: closed houring). The housing has an opening (9) for pressing on the wiping surface (13). The wiping material (13) is provided on a carrier (11) and fixed to a hinge (14) of the housing. The carrier can be flipped open to do the wiping and in order to press the wiping surface onto the opening (9) of the test strip housing, it is closed again, if necessary, arrested in its position. Contact between the wiping surface and the test strip surface can be accomplished either manually or with the aid of a clamp.

In the next step, liquid eluant is applied onto the application zone (1). The liquid can either be applied directly onto the application zone, or the test strip can be immersed into the eluant. If the liquid is applied, the application zone is preferably made of a particularly well-absorbing material which should absorb at least so much liquid that the liquid migrates to the end of the chromatography strip. If the test carrier is provided in a housing, the housing preferably has an opening (7) where liquid can be applied.

Possible eluting liquids are water or buffer solution that are conventionally used in immunoassays. The liquid travels along the strip in direction toward the target zone (4) while passing the zone with a pressed-on wiping surface. Surprisingly, it has been found that the analyte molecules adhering to the wiping surface are taken up in the liquid flow and transported to the following zones. It is preferred when the zone of the test strip onto which the wiping fleece is pressed ("uptake zone") is made of a material that is preferably used for the wiping fleece. It is particularly preferred when the uptake zone consists of the conjugate zone (2) itself.

In a preferred variant of the test, analyte molecules form a complex with labeled analyte-binding partners when passing the conjugate zone. Labeled binding partners that do not form a complex are retained in the capture zone by immobilized analyte analogs, e.g. polyhaptens. Labeled binding partners that are bound to an analyte pass the capture zone and reach the target zone. In the target zone, the labeled complexes can then be detected. For a better optical differentiation between the signal and the target zone and the label in the capture zone, the latter can advantageously be covered. When the test carrier is provided in a housing, said housing preferably has an opening (10) above the target zone to monitor the signal.

The analysis for an analyte contamination of the surface to be examined is considered positive when at least a partial area of the target zone shows a coloration. This coloration can easily be detected visually or photometrically.

It is also possible to detect several analytes with one single test strip device. To achieve this, conjugate zone and capture zone and, if necessary, also the chromatographic material extending from the conjugate zone to the target zone, can be divided into several partial strips that run parallel to the actual test strip and are advantageously separate from one another. In the individual partial conjugate zones and partial capture zones, there are binding partners for the different analytes or analyte analogs to be detected. Upon contact of the wiping surface with a preferably common uptake zone preceding the conjugate zone and before applying the eluant, the analyte liquid in the different partial conjugate zone is allotted to the different partial chromatographic migration paths, with a different analyte being detected in each partial target zone.

Surprisingly, it has been found that the sensitivity of the method of the invention is significantly higher than that of the prior art. The efficiency of the wiping and transfer of analyte from the wiping surface onto the test strip is against all expectations so high that this method allows the detection of absolute amounts of down to 10 ng of analyte, especially drugs on surfaces. The method involves less handling steps and the result can be determined in a very rapid and simple manner.

Another subject matter of the invention is a test kit for detecting surface contamination by an analyte in an immunological detection reaction, characterized in that it comprises the following:

a) a test strip made of one or several capillary chromatographic planar materials that are in fluid contact with one another comprising
    an eluant application zone at its one end and a target zone at its other end,
    a capture zone between the eluant application zone and the target zone where a capture reagent is immobilized, said capture reagent being capable of specifically binding either the analyte, a specific analyte-binding partner, or a labeled binding partner, and a conjugate zone between the eluant application zone and the capture zone containing a migratable labeled binding partner, said binding partner being capable of specifically binding either the analyte, the specific analyte-binding partner, or the capture reagent while the binding of the labeled binding partner generates a detectable signal in the capture zone or the target zone indicating the presence of the analyte, b) a wiping surface that is separated from the test strip surface, c) a pressing device to establish a planar contact between the wiping surface and the area between the application zone and the conjugate zone, or preferably with the conjugate zone itself.

EXAMPLE 1 a. Preparation of Benzoylecgoninmaleimidoethylamide 1 g N-hydroxysuccinimide and 1.8 g dicyclohexylcarbodiimide are added to 2.4 g bencoylecgoninhydrochloride in 200 ml dry acetonitril and stirred for 3 hours. The precipitate is removed via filtration, the filtrate is concentrated, taken up in nitromethane and again filtered. After concentrating the solvent, the mixture is triturated with ether. The result are 1.13 g benzoylecgoninsuccinimidyl ester. This product is taken up in 100 ml dry acetonitrile together with 0.47 g maleimidoethylaminehydrochloride (see WO 90/15798). Then 1.1 g triethylamine are added and stirred for 12 hours at room temperature. The reaction mixture is concentrated, taken up in 50 ml acetic ester and extracted three times with sodium hydrogen carbonate solution. The acetic ester phase is concentrated and the product is converted into hydrochloride by adding it to 10 ml HCl saturated dioxane. The mixture is then filtered and washed with ether. The result is 1 g benzoylecgoninmaleimidoethylamidehydrochloride.

b. Preparation of a Biotinylated Cocaine Polyhapten for the Capture Zone

At a concentration of 25 mg/ml in phosphate buffer, pH 8, rabbit IgG is reacted with a 6-fold molar amount of S-acetylthiopropionic acid succinimidylester dissolved in dimethylsulfoxide. After 1 hour at 25° C., the reaction is stopped by adding a solution of 1 mol/l lysine. Then a dialysis against 0.1 mol/l potassium phosphate buffer, pH 6 with 1 mmol/l EDTA is carried out. Subsequently, the pH is adjusted to 7.8 and incubated with 1 mol/l hydroxylamine solution, pH 7.5 at 20 mmol/l for 1 hour at 25° C. For the coupling, a five-fold molar excess of benzoylecgoninmaleimidoethylamidehydrochloride dissolved in dimethylsulfoxide and is added under stirring to the solution of the rabbit IgG modified with sulfhydryl groups. After incubation at 25° C. for 2 hours, the reaction is stopped by successively adding 0.1 mol/l cystein solution ad 1 mmol/l and 0.5 mol/l iodineacetic amide solution at 5 mol/l. The batch is dialyzed overnight against 0.1 mol/l potassium phosphate buffer, pH 8.5 and concentrated to a protein concentration of 10 mg/ml by means of membrane filtration. Subsequently, the resulting cocaine polyhapten is biotinylated with an eight-fold molar excess of biotinylcaproic acid succinimidylester, dissolved in dimethylsulfoxide. The batch is dialyzed against 20 mmol/l sodium acetate, pH 4.3, and purified via FPLC.

c. Preparation of Morphino-3-O-acetic Acid Maleimidoethylamidehydrochloride

Morphino-3-O-acetic acid is converted to morphino-3-O-acetic acid maleimidoethylamidehydrochloride using maleimidoethylaminehydrochloride as described for example 1a.

d. Preparation of a Biotinylated Morphine Polyhapten

As described for example 1b, rabbit IgG modified with sulfhydryl groups is reacted to a biotinylated morphine polyhapten using morphino-3-O-acetic acid maleimidoethylamidehydrochloride and biotinylcaproic acid succinimidylester.

e. Preparation of a Gold Conjugate from an Anti-cocaine Antibody

Goldsol with a particle diameter of 20 nm determined via photon correlation spectroscopy was manufactured according to standard procedures (Frens., Nature Vol. 241, p. 20–22, 1973). Conjugation with the antibody that recognizes cocaine and benzoylecgonin was carried out according to prior art procedure (Geoghegan et al., J. Immunol. Meth. Vol. 34, p. 11–31, 1980).

f. Preparation of a Gold Conjugate from an Anti-morphine Antibody

As described for example 1e, an antibody that recognizes morphine and heroine was bound to gold particles.

EXAMPLE 2 a. Test Carrier for the Determination of Cocaine

The structure of the test carrier is described in FIG. 1.

Eluant Application Zone (Absorbing Fleece) (1)

The polyester fleece used was manufactured by Binzer, Hatzfeld, Federal Republic of Germany. The fleece is a pure polyester fleece reinforced with 10% curalon. The thickness ranges between 0.1 and 0.2 mm, the absorbance capacity is 1800 ml/m$^2$.

Conjugate Zone (Conjugate Fleece) (2)

A mixed fleece consisting of 80 parts polyester and 20 parts viscous staple fibers, reinforced with 20 parts curalon at a thickness of 0.32 mm and a absorbing capacity of 500 ml/m$^2$ is impregnated with the following solution and then dried: 100 mmol/l HEPES buffer, pH 7.5, 100 mol/l NaCl, conjugate of gold particles and an anti-cocaine antibody that also binds to benzoylecgonin at a concentration that has an optical density of 10 at 520 nm.

Capture Zone (3)

A fleece consisting of 100% linters, reinforced with 2% etadurin with a thickness of 0.35 mm and an absorbing capacity of 372 ml/m$^2$ is impregnated with the following solution and then dried: 10 mmol/l sodium phosphate pH 7.5, polymerized streptavidin 200 mg/l (manufactured according to example 1c, EPS 0 331 127).

The pre-impregnated fleece is then once more impregnated and also dried again: 10 mmol/l sodium phosphate pH 7.5, 200 mg/l biotinylated cocaine polyhapten of example 1b.

Detection Field (Target Zone) (4)

The fleece used consists of 100% linters, reinforced with 2% etadurin with a thickness of 0.35 mm and an absorbing capacity of 372 ml/m$^2$.

All fleeces have a width of 5 mm. The conjugate fleece is 5×5 mm in size. The fleeces are glued onto a carrier foil (5) of 5 mm in width according to FIG. 1.

b. Test Carrier for the Detection of Heroine

A test carrier for the detection of heroine is manufactured correspondingly from the gold conjugate of the anti-heroine antibody and the biotinylated morphine polyhapten.

EXAMPLE 3

Portions of 10 μl of a diluted heroine hydrochloride solution in methanol are applied onto a polyethylene surface and allowed to dry. The results are areas of approx. 1 cm$^2$ in size contaminated with 10, 20, 40, 60, and 80 ng heroine hydrochloride, respectively. Three test fields are prepared from of each amount.

A fleece was prepared consisting of 80 parts polyester fibers with a fiber density of 3.3 dtex and a fiber length of 4 mm, 20 parts viscous staple fiber with a fiber density of 1.7 dtex and a length of 3 mm, and 20 parts polyvinyl alcohol fibers with a length of 4 mm. The materials polyester, viscous staple fiber and polyvinyl alcohol were separated in a mixing tub with fully deionized water at a material density of 0.3%. The fiber material was then pumped into a rotary sieve. While water was removed from the fiber mixture, i.e. the water being evacuated, the fibers aligned themselves on the sieve side and contact-dried via a drying cylinder as a fleece with a dry content of 20%. The result is a fleece with a basis weight of 80 g/m² and a thickness of 0.32 mm.

Pieces of 5×5 mm of this fleece (2) were then glued onto a carrier (5) as shown in FIG. 1. The wiping fleece now mounted to a carrier was used to wipe over test fields contaminated with heroine.

A wiping fleece mounted on the carrier was positioned over the conjugate fleece of the test carrier manufactured according to example 2b. It was pressed on by applying minimum pressure and fixed in its position with a clamp.

The eluant application zone is immersed into a chromatography buffer (150 mmol/l NaCl, 50 mmol/l potassium phosphate buffer pH 7.2) for 5 seconds. It is then placed on a non-absorbent support and after 2 minutes, the coloration (C-value) is determined with a chromameter manufactured by Minolta. Then, a visual check of the detection field for the presence of a pink coloration is carried out.

| Amount of heroine Test field [ng] | C-value | Visual reading[1] |
|---|---|---|
| 0 | 3.36 | 0 |
| 10 | 2.99 | 0 |
| 10 | 3.05 | 0 |
| 10 | 3.30 | 0 |
| 20 | 7.88 | + |
| 20 | 9.46 | + |
| 20 | 6.89 | +/− |
| 40 | 5.68 | +/− |
| 40 | 8.74 | + |
| 40 | 11.35 | + |
| 60 | 12.00 | ++ |
| 60 | 10.31 | + |
| 60 | 15.05 | ++ |
| 100 | 14.17 | ++ |
| 100 | 10.26 | + |
| 100 | 16.85 | ++ |

[1]0: no pink coloration in the detection field
+/−: week coloration
+: normal coloration
++: strong coloration

EXAMPLE 4

With diluted cocaine solution in water, test areas with 5, 10, 25, 50, 75 and 100 ng cocaine, respectively, were applied onto a polyethylene foil corresponding to example 3. Also corresponding to example 3, a device according to diagram 2 containing test carriers according to example 2a for the determination of cocaine were used to wipe off the test areas. The wiping fleeces have a round shape and a diameter of 4 mm. The detection field was subject to a visual check for pink coloration.

| Amount of cocaine/ test field [ng] | Visual reading[2] |
|---|---|
| 0 | 0 |
| 5 | +/− |
| 10 | +/− |
| 25 | + |
| 50 | ++ |
| 75 | ++ |
| 100 | ++ |

[2]0: no pink coloration in the detection field
+/−: weak coloration
+: normal coloration
++: strong coloration

EXAMPLE 5

One part cocaine is mixed with 1000 parts lactose. 5 mg of this mixture were distributed over an area of 220 cm² of a cotton cloth. Approximately 10 m² of this area were wiped according to Example 4 and analyzed. In all tests, a pink coloration in the detection field was visually detected. Correspondingly, a polyethylene foil of 2 cm² was contaminated with cocaine containing particles and subject to analysis by wiping. A pink coloration could again be visually detected in the detection field in all experiments.

EXAMPLE 6

10 μl of the correspondingly diluted solution of cocaine hydrochloride in water was applied onto a rough anodized aluminum plate and distributed over an area of 1 cm². After drying at 37° C. of 15 min, the contaminated areas were wiped with a round fleece according to Example 3 with a diameter of 5 mm while a minor pressure was applied. The wiping is carried out without wetting (dry) and with a fleece that had been wetted with 2 μl of water before the procedure. The wiping fleeces were then placed on the respective conjugate zone of a test carrier to detect cocaine according to sample 3 and fixed with a flat pair of tweezers. Half of the absorbing fleece of the test carriers was immersed into water for 10 seconds. Subsequently, a test carrier was placed on a flat, non-absorbent support and the color in the detection field was determined after 2 minutes.

| Absolute amount of cocaine hydrochloride in the test field [ng] | Visual reading after wiping with a dry wiping fleece[3] | Visual reading after wiping with a wet fleece |
|---|---|---|
| 1000 | ++ | ++ |
| 600 | ++ | ++ |
| 300 | + | ++ |
| 200 | + (minor) | ++ |
| 100 | 0 | ++ |
| 60 | 0 | ++ |
| 30 | 0 | ++ |
| 25 | 0 | ++ |
| 16 | 0 | ++ |
| 8 | 0 | + |
| 4 | 0 | 0 |

[3]0: no pink coloration in the detection field
+: normal coloration
++: strong coloration

What is claimed is:
1. A method for detecting contamination of a surface by an analyte, comprising:

wiping the surface to be tested with a wiping surface;

providing a capillary active, chromatographic test strip having a planar surface and two ends, with an eluant application zone proximate one end and a target zone proximate the other end, and being in fluid communication therebetween; thereafter contacting the planar surface of the test strip in an area between the eluant application zone and the target zone with the wiping surface forming a site of contact;

applying eluant onto the eluant application zone to cause the eluant to move toward the target zone and past the site of contact while maintaining contact of the planar surface in said area by the wiping surface in order to take up analyte in the eluant and to move the analyte to the target zone; and thereafter measuring in the target zone an immunological binding reaction to detect the analyte.

2. Method of claim 1, wherein the test strip has a capture zone, wherein a capture reagent is immobilized, between the eluant application zone and the target zone, the capture reagent being a specific binding partner for the analyte, a specific binding partner for the analyte binding partner, or a specific binding partner for a labeled binding partner, and wherein the test strip further has a conjugate zone between the eluant application zone and the capture zone, the conjugate zone having a migratable, labeled specific binding partner for (a) the analyte, (b) a specific analyte binding partner, or (c) the capture reagent, the method including the step of capillarily passing the eluant through the conjugate zone and the capture zone to produce a detectable signal in the capture zone or in the target zone, which signal indicates the presence of the analyte on the tested surface.

3. Method of claim 2, wherein the area of contact of the wiping surface with the test strip is between the eluant application zone and the conjugate zone.

4. Method of claim 2, wherein the area of contact of the wiping surface with the test strip is the conjugate zone.

5. Method of claim 2, including the step of applying a migratable analyte-binding partner, having a binding site for the capture reagent, to the test strip between the eluant application zone and the capture zone.

6. Method of claim 2, wherein a labeled binding partner for an analyte is in the conjugate zone, and an immobilized analyte analog is in the capture zone, and the label passing the capture zone is detected in the target zone to determine the presence of the analyte.

7. Method of claim 2, wherein the labeled binding partner has a metal label.

8. Method of claim 7, wherein the metal is gold.

9. Method of claim 1, wherein the analyte is a controlled substance drug molecule or particle.

10. Method of claim 1, wherein the wiping surface is a surface of a fleece.

11. Method of claim 10, wherein the fleece contains fibers of cellulose and/or polyester.

12. Method of claim 1, wherein the step of contacting the test strip surface with the wiping surface is conducted with the aid of a contact pressure device.

13. Method of claim 1, wherein the wiping surface is wetted with a liquid.

14. Method of claim 13, wherein the liquid is an aqueous buffer.

15. Method of claim 13, wherein the liquid contains detergent and/or at least one organic solvent.

16. Method of claim 13, wherein the liquid is an organic solvent.

17. Method of claim 13, wherein the liquid is water.

18. A test kit for detecting surface contamination by an analyte by an immunological detection reaction, the test kit comprising a) a test strip made of at least one capillary active chromatographic planar material and having a surface and an end which is in fluid communication with another end, and comprising an eluant application zone at one end and a target zone at the other end, with a capture zone therein between containing a capture reagent immobilized therein, the capture reagent capable of specifically binding the analyte, a specific analyte-binding partner, or a labeled binding partner, and a conjugate zone located between the eluant application zone and the capture zone and containing a migratable labeled binding partner which is capable of specifically binding the analyte, a specific analyte-binding partner or the capture reagent, with the binding of the labeled binding partner generating a detectable signal in the capture zone or the target zone to indicate the presence of the analyte, b) a wiping surface which is separated from the test strip surface, and c) a contact pressure means for establishing planar contact between the wiping surface and an area which is between the application zone and the conjugate zone, or between the wiping surface and the conjugate zone.

19. Test kit of claim 18, wherein a labeled specific binding partner for the analyte is in the conjugate zone, and an immobilized analyte analog is in the capture zone.

20. Test kit of claim 19, wherein the wiping surface is the surface of a fleece.

21. Test kit of claim 20, wherein the fleece is made of fibers of cellulose and/or polyester.

22. A method of detecting the presence of a controlled substance on a surface to be tested comprising a) wiping the controlled substance off of the surface with a wiping surface;

b) providing a capillary active, chromatographic test strip having a planar surface and two ends which are in fluid communication, the test strip having an eluant application zone proximate one end, a target zone proximate the other end, and a capture zone thereinbetween, a capture reagent capable of specifically binding the controlled substance, a specific controlled substance-binding partner, or a labeled binding partner being immobilized in the capture zone, and a conjugate zone, containing a migratable labeled specific binding partner for the controlled substance, a specific controlled substance-binding partner, or the capture reagent, located between the eluant application zone and the capture zone;

c) contacting the planar surface of the test strip in the conjugate zone or in an area between the eluant application zone and the conjugate zone with the wiping surface having the controlled substance thereon forming a site of contact to transfer the controlled substance to the test strip;

d) applying liquid eluant to the test strip at the eluant application zone in an amount sufficient for the eluant to move by capillary action from the eluant application zone toward the target zone and past the site of contact of the test strip with the wiping surface while maintaining contact of the planar surface in said site by the wiping surface in order to take up controlled substance in the eluant and to move the controlled substance to the target zone; and e) detecting in the capture zone or in the target zone a detectable signal caused by an immunological binding reaction involving the controlled substance, with the detectable signal indicating the presence of the controlled substance on the tested surface.

23. Method of claim 22, wherein the controlled substance is cocaine, morphine or heroin.

24. Method of claim 22, wherein the immunological binding reaction is a sandwich immunoassay.

25. Method of claim 22, wherein the immunological binding reaction is a competitive immunoassay.

* * * * *